United States Patent [19]

Broussard et al.

[11] Patent Number: 4,876,368

[45] Date of Patent: Oct. 24, 1989

[54] PRODUCTION OF MONOHYDROXY MONOCYCLIC ACETALS AND THEIR ESTERS

[75] Inventors: Jerry A. Broussard, Summit, N.J.; Wayne C. Fuqua, Boulder, Colo.; James H. George, Portland, Tex.

[73] Assignee: Hoechst Celanese Corporation, Bridgewater, N.J.

[21] Appl. No.: 197,936

[22] Filed: May 24, 1988

[51] Int. Cl.$^4$ .................. C07D 319/06; C07D 317/20; C07D 321/06

[52] U.S. Cl. .................................. 549/374; 549/375; 549/372; 549/370; 549/347; 549/453; 549/454

[58] Field of Search ............... 549/453, 347, 454, 370, 549/372, 374, 375

[56] References Cited

U.S. PATENT DOCUMENTS 4,076,727 2/1978 Zey et al. ............................ 549/372
4,207,155 6/1980 Martin et al. .................. 204/159.23

FOREIGN PATENT DOCUMENTS 0165164 12/1925 European Pat. Off. .
1166366 10/1969 United Kingdom .

Primary Examiner—Nicky Chan
Attorney, Agent, or Firm—Marvin Turken

[57] ABSTRACT

A process is provided for the production of a monohydroxy monocyclic acetal, e.g., trimethylolpropane cyclic formal, of a trihydroxy alcohol, e.g., trimethylolpropane, and an aldehyde, e.g., formaldehyde, by subjecting a "heavier condensation product" of the trihydroxy alcohol and the aldehyde than the desired cyclic acetal, i.e., one having a higher molecular weight and boiling point, to acetal formation conditions. In a preferred embodiment, the product of reaction of the trihydroxy alcohol and aldehyde is treated to remove the desired monohydroxy monocyclic acetal product and at least part of the remainder comprising the heavier condensation product is recycled to the reaction together with a flesh supply of trihydroxy alcohol and aldehyde. The monohydroxy monocyclic acetal product may be further reacted to obtain a desired ester, e.g. trimethylolpropane cyclic formal acrylate, such as by transesterifying the acetal with a low boiling ester of the esterifying acid, e.g., methyl acrylate, using tetra-isopropyl orthotitanate as transesterification catalyst.

12 Claims, No Drawings

PRODUCTION OF MONOHYDROXY MONOCYCLIC ACETALS AND THEIR ESTERS

BACKGROUND OF THE INVENTION

1. Field of the Invention

This invention relates to improved processes for the production of monohydroxy monocyclic acetals and their esters, e.g. trimethylolpropane cyclic formal (TMPF), and its acrylate ester (THPFAcA).

2. Background of the Invention

Monohydroxy monocyclic acetals and certain of their esters are known in the art. Thus, U.S. Patents Nos. 4,076,727 issued Feb. 28, 1978 to Zey et al., and 4,207,155 issued June 10, 1980 to Martin et al., disclose the production of monohydroxy monocyclic acetals by reacting a trihydroxy alcohol selected from the group consisting of trimethylolpropane (TMP), trimethylolethane (TME), and compounds having the formula:

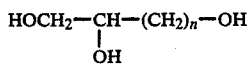

where n is 1 to 4, e.g., glycerin, with an aldehyde selected from the group consisting of formaldehyde or a formaldehyde source, $C_2$-$C_4$ aldehydes, e.g. butyraldehyde, and $C_2$-$C_4$ halogenated aldehydes, e.g., chloral. As an illustration of this reaction, Example 1 of each of the cited patents shows the reaction of trimethylolpropane with formaldehyde in the presence of benzene using para-toluenesulfonic acid as catalyst to produce a crude product. The latter is then refluxed to remove water, cooled, extracted to remove catalyst, dried, solvent stripped to remove benzene, and distilled under vacuum to obtain an 87% by weight yield of what is assumed to be the monohydroxy monocyclic trimethylolpropane formal. (TMPF).

After formation of the monohydroxy monocyclic acetal, e.g., TMPF, it may be formed into an ester, e.g., an acrylate or methacrylate ester using one of the three methods disclosed in Patent No. 4,207,155, viz., transesterification with a low boiling ester containing the desired acid moiety, e.g., ethyl acrylate, using a transesterification catalyst, e.g., a titanium ester; reaction with acryloyl chloride or methacryloyl chloride; or direct esterification with acrylic or methacrylic acid using an acidic acetal formation catalyst. The monocyclic acetal acrylates and methacrylates are stated in Patent No. 4,076,727 to be "useful in practically any end use where vinyl polymerizable monomers are utilized. In addition, they are particularly useful as diluents in unsaturation-containing coatings, particularly as diluents in ultraviolet curable coating compositions."

Also of interest is British patent No. 1,166,366 which discloses various means for the formation of cyclic acetal esters including reaction of a cyclic acetal alcohol with a halide or anhydride of the esterifying acid in the presence of an equivalent amount of a base such as pyridine, or reaction of the cyclic acetal with the esterifying acid or its anhydride in the presence of a separate, strongly acidic catalyst; and European Patent Application Publication No. 165,164 which teaches on pages 6 and 7 the acylation of mixed glycerol formals with acetic anhydride in the presence of pyridine.

SUMMARY OF THE INVENTION

In accordance with this invention, a monohydroxy monocyclic acetal of a trihydroxy alcohol selected from the group consisting of trimethylolpropane, trimethylolethane and compounds of the formula:

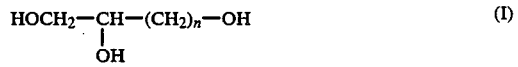

where n is 1 to 4, e.g., glycerin, with an aldehyde having the formula:

where R' is hydrogen, $C_1$-$C_3$ alkyl, or $C_1$-$C_3$ halogenated alkyl, is produced by subjecting a composition comprising at least one added "heavier condensation product" of said trihydroxy alcohol and said aldehyde than said monohydroxy monocyclic acetal, i.e., a condensation product having a higher molecular weight and higher boiling point than said monocyclic acetal, to acetal formation conditions.

As shown in the cited U.S. Pat. Nos. 4,076,727 and 4,207,155, the entire disclosures of which are incorporated by reference, the condensation of a contemplated trihydroxy alcohol with an aldehyde of Formula (II) results in the formation of at least one monohydroxy monocyclic acetal primarily of the following formulas (III), (IV), or (V).

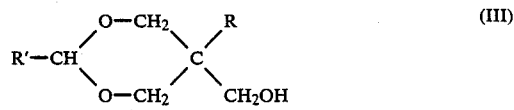

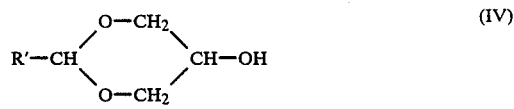

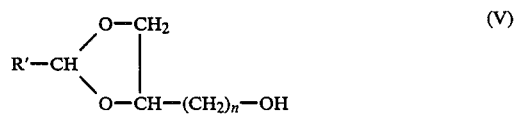

wherein R is ethyl or methyl, and R' and n are as previously defined. Thus, an acetal of Formula (III) results from the condensation of TMP or TME with an aldehyde, an acetal of Formula (IV) results from the condensation of the hydroxyl groups on the first and third carbon atoms of glycerin with an aldehyde, and an acetal of Formula (V) results from the condensation of the hydroxyl groups of the first and second carbons of any of the trihydroxy alcohols of Formula (I) with an aldehyde. In the case of glycerin, a mixture of acetals of Formulas (IV) and (V) is obtained, where n in Formula (V) is 1.

It has been found, however, that when a trihydroxy alcohol and an aldehyde of the defined groups are subjected to acetal formation conditions as disclosed in the previously cited patents, not only a desired monohydroxy monocyclic acetal of Formulas (III), (IV), or (V) is produced. Rather, a significant though minor amount, e.g., on the order of about 10–20% of the theoretical yield of monohydroxy monocyclic acetal, of heavier condensation products are also produced. Moreover, if such heavier condensation products are discarded, the result is a reduction in the overall yield of desirable monohydroxy monocyclic acetal product, which constitutes an economic detriment to the process.

It has further been found that if a composition comprising at least some of the foregoing heavier condensation products in the feed mixture, is subjected to acetal formation conditions similar to those to which the trihydroxy alcohol and aldehyde of the specified groups are subjected to in producing the desired monohydroxy monocyclic acetal, the result is a reequilibration of the mixture and the formation of a reconstituted equilibrium mixture. Moreover, such reconstituted mixture contains the desired monohydroxy monocyclic acetal and heavier condensation productions in almost the same amounts as those obtained on condensation of the original trihydroxy alcohol and aldehyde, e.g. about 80% of the theoretical yield of the desired monohydroxy monocyclic acetal and about 20% of heavier condensation products, based on the total combined and uncombined trihydroxy alcohol and aldehyde moieties present, including those of the initially present heavier condensation product as well as those of any monohydroxy monocyclic acetal also initially present, and any freshly added free trihydroxy alcohol and aldehyde. Thus, in the formation of the desired monohydroxy monocyclic acetal by reaction of the trihydroxy alcohol and aldehyde, it is possible to take advantage of the described reequilibration effect and raise the overall yield of desired product by recycling to the reaction at least some of the heavier condensation products remaining after the desired monohydroxy monocyclic acetal is separated from the reaction mixture. It should be noted that the benefit of this effect is obtained whether the heavier condensation products being reacted to produce additional monohydroxy monocyclic acetal are present in the initial feed mixture in an amount greater than, equal to, or less than the equilibrium amount which results from the reaction of all components of the composition including any free trihydroxy alcohol, free aldehyde, and monohydroxy monocyclic acetal also present. As pointed out previously, such equilibrium amount of heavier condensation products generally contains about about 10-20% of the total trihydroxy alcohol and aldehyde moieties present in the composition in both free and combined form.

After obtaining the monohydroxy monocyclic acetal separated from the heavier condensation products present in the product, a desired ester of such acetal may be obtained using any of the methods disclosed in U.S. Pat. No. 4,207,155, viz., transesterification, reaction with an acid halide, direct esterification with the free acid, or by other methods, such as reaction of the acetal with the anhydride of the esterifying acid in the presence of pyridine.

DESCRIPTION OF SPECIFIC EMBODIMENTS

The contemplated trihydroxy alcohols used to produce the desired monohydroxy monocyclic acetals and heavier condensation products are, in addition to trimethylolpropane, trimethylolethane and glycerin, 1,2,4-butanetriol, 1,2,5-pentanetriol, and 1,2,6-hexanetriol. The preferred trihydroxy alcohol is trimethylolpropane (TMP).

Some contemplated aldehydes in addition to formaldehyde which may be used in the formation of the desired monohydroxy monocyclic acetal and heavier condensation products are, for example, acetaldehyde n-propionaldehyde, n-butyraldehyde and chloral. The preferred aldehyde is formaldehyde, which may be added in gaseous form, as an aqueous (formalin) or alcoholic solution, or as obtained from a polymer such as paraformaldehyde or trioxane. In the case of the condensation of TMP with formaldehyde, the desired monohydroxy monocyclic acetal product, viz., TMPF, has the formula:

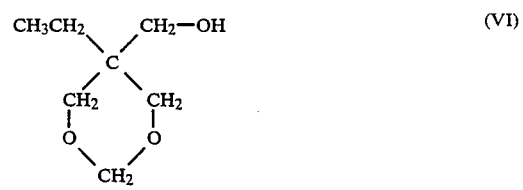

In carrying out the process of this invention, a composition comprising the heavier condensation product of the contemplated trihydroxy alcohol and aldehyde as previously described is contacted with an acetal formation acid catalyst, e.g., sulfuric acid, methanesulfonic acid para-toluenesulfonic acid, benzenesulfonic acid, acidic ion-exchange catalysts, e.g., sulfonic acid ion-exchange catalysts and the like, at a temperature up to about 150° C., and preferably below about 120° C. for a period of about 1 to 20 hours. Preferably, the reaction feed composition also contains a fresh supply of the trihydroxy alcohol and about 0.5 to 1.2 mole of aldehyde per mole of trihydroxy alcohol, and about 15 to 90 wt.% based on the total composition of a reflux solvent having a relatively low boiling point, preferably below 150° C., more preferably below about 115° C. at atmospheric pressure, e.g. benzene, toluene, xylenes, hexane, cyclohexane, or mixtures of these solvents. The resulting composition is refluxed, e.g., at about 60° C. to 130° C., to remove the water of reaction, and extracted with an aqueous alkali metal carbonate, bicarbonate or hydroxide solution to remove the catalyst. The reflux solvent is then distilled at reduced pressure, e.g., at a temperature below about 150° C. and a pressure of about 100 to 300 mm Hg absolute. After removal of most of the reflux solvent, the mixture is subjected to distillation at increased vacuum, e.g., at a temperature of about 130° to 136° C. and a pressure of about 20 mm Hg absolute to remove the desired monohydroxy monocyclic acetal product. The remaining heavier condensation products are then subjected to the same reaction conditions as described, preferably as recycle with additional feed of trihydroxy alcohol and aldehyde.

As pointed out previously, the condensation of trihydroxy alcohol, e.g., TMP, with aldehyde, e.g., formaldehyde, results in the formation of about 10-20% of the theoretical yield, of heavier condensation products in addition to the desired monohydroxy monocyclic acetal, e.g. TMPF. In the case of the condensation of TMP and formaldehyde, gas chromatography (GC) and nuclear magnetic resonance (NMR) analysis of such heavier condensation products indicate that one of the products is the bis-cyclic monolinear formal of TMP having the formula:

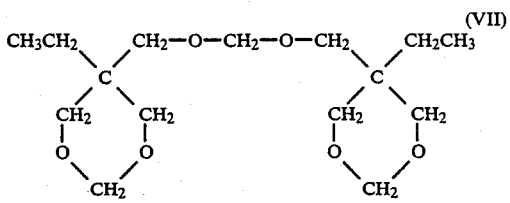

It is believed that other heavier condensation products of TMP and formaldehyde have the formulas of the monocyclic linear condensation product of two moles of TMP and two moles of formaldehyde [Formula (VIII)] and the acyclic condensation product of two moles of TMP and one mole of formaldehyde [Formula (IX)]:

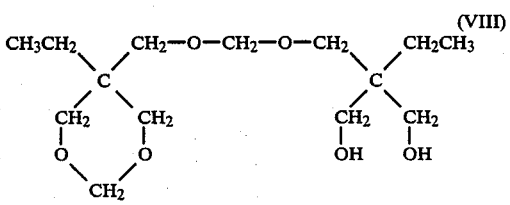

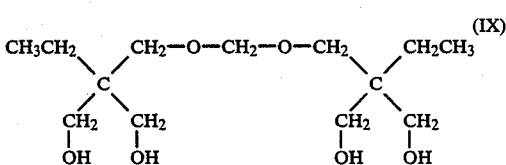

In the case of condensation of a contemplated trihydroxy alcohol and/or aldehyde other than TMP and/or formaldehyde, the formulas of the heavier condensation products are believed to be analogous to the foregoing formulas for heavier condensation products of TMP and formaldehyde, with the various chemical groups corresponding to those in the original trihydroxy alcohol and aldehyde condensed to form the desired monohydroxy monocyclic acetal.

While it is possible to practice the process of this invention by subjecting a reactable material consisting of heavier condensation products of the contemplated trihydroxy alcohol and aldehyde to an acetal formation reaction as previously defined, it is preferable to react such heavier condensation product admixed with a supply of trihydroxy alcohol and aldehyde mixed in free form with the heavier condensation product. Thus, for example, the heavier condensation product remaining as a residue after the separation of water and desired monohydroxy monocyclic acetal from the reaction mixture, may be recycled to the reaction zone where it is mixed with a new supply of trihydroxy alcohol and aldehyde. Such a process including the reaction of a mixture containing a fresh supply of trihydroxy alcohol and aldehyde mixed with recycled heavier condensation product, separation of water of reaction and desired monohydroxy monocyclic acetal, and reaction of the remaining heavier condensation product mixed with the additional supply of trihydroxy alcohol and aldehyde, can be practiced in a continuous (using swing vessels), semi-continuous, or batch operation.

A desired ester of a contemplated monohydroxy monocyclic acetal with an appropriate acid may be prepared from the acetal using any of the methods disclosed in U.S. Pat. No. 4,207,155, viz. transesterification with an ester of the acid with a low boiling alcohol in the presence of a transesterification catalyst, reaction with an acid halide or acid anhydride of the acid, e.g., the latter in the presence of a base such as pyridine, or direct esterification with the acid in the presence of an acidic esterification catalyst. The esterifying acid may be for example an unsaturated acid, e.g., acrylic or methacrylic acid, or saturated, e.g., an alkanoic acid containing, for example, 1 to 10 carbon atoms. The preferred method of preparing the ester, particularly the ester of acrylic or methacrylic acid, is by transesterifying the contemplated monohydroxy monocyclic acetal with an alkyl ester of the appropriate acid wherein the alkyl groups contain 1 to about 4 carbon atoms, using tetra-isopropyl orthotitanate as a transesterification catalyst. A by-product of the transesterification reaction is the alkanol corresponding to the alkyl groups of the transesterifying ester. When an acrylate ester of the contemplated cylic acetal is being produced by transesterification with methyl acrylate, the by-product is methanol which comes off from the reaction mixture as an azeotrope with methyl acrylate. In general, the transesterification is carried out by reacting the acetal with about 1.0 to 10 moles of alkyl ester at a temperature of about 50° to 150° C. for a period until little or no by-product lower alkanol is given off, generally about 1 to 20 hours, using about 0.1 to 5.0 wt.% of catalyst.

Another preferred method of preparing the foregoing esters is reaction of the cyclic acetal with the anhydride of the esterifying acid in the presence of a base such as pyridine.

When an ester of a cyclic acetal with an unsaturated acid such as acrylic or methacrylic is produced by transesterification, or direct esterification with the acid, an inhibitor such as the methyl ether of hydroquinone (MEHQ) or any of the inhibitors disclosed in col. 3 of U.S. Pat. No. 4,207,155 is generally added to prevent or minimize polymerization during the reaction.

The following examples collectively illustrate the process of this invention.

EXAMPLES 1 TO 6

In these examples, trimethylolpropane cyclic formal (TMPF) was prepared by reacting either trimethylolpropane (TMP) with formaldehyde (HCHO) from paraform (Example 1), a mixture of heavier condensation products of TMP and HCHO than TMPF, which were formed in the previous example, together with freshly added TMP and HCHO from parafrom (Examples 2 and 3), heavier condensation products without any freshly added TMP or HCHO (Example 4 and 5), or heavier condensation products with only freshly added TMP (Example 6). The reaction was carried out in refluxing benzene as reaction solvent and was driven to completion by azeotropic removal of the water of reaction, using methanesulfonic acid (MSA), as the acidic catalyst. The apparatus employed included a 12-liter flask equipped with a heating mantle, thermowell, mechanical stirrer, 10 tray by 3 in. Oldershaw column, phase separator and reflux condenser. A 12-liter flask equipped with a heating mantle, mechanical stirrer, and a bottom draw-off port was used for the neutralization and phasing steps. A one-plate flash distillation apparatus was used to remove the benzene solvent and for the final vacuum distillation of TMPF.

The reactants as described together with MSA as a 70% aqueous solution and benzene solvent were charged into the reactor. The reaction mixture was heated and stirred while the water of reaction was removed overhead as the benzene azeotrope, with the reaction being carried out between 80°-95° C. in the refluxing benzene. Boil-up rate was approximately 0.8% of the total reaction charge per minute. The reaction progress was followed by measuring the amount and rate of water formation. After typical reaction times of 5½ to 6½ hours, the rate of water formation dropped to about 1% of the theoretical total per hour, and a theoretical amount of water had been collected overhead.

The MSA catalyst was neutralized with a 20% excess of 13% aqueous $Na_2CO_3$. Phasing was accomplished after 1 hour at 45°-50° C. The lower aqueous layer was drawn off and discarded. Traces of neutralized salts were removed from the organic phase with a 100 gram water wash, with the phasing requiring 30 minutes at 45°-50° C. The organic phase was transferred to a one-plate vacuum distillation apparatus where a majority of the benzene was flashed off at 100-130 mm Hg pressure. Base temperature was maintained below 150° C.

After benzene removal, the pressure was dropped to 20 mm Hg for distillation of the product. Following a small riser cut (base <140° C.; overhead <130° C. at 20 mm Hg), the product was collected at 130°-136° C. (base 140°-15° C., 20 mm Hg). The temperature in the base was not allowed to exceed 165° C. to minimize thermal decomposition of the product.

The amounts of grams of freshly charged material, recycled material and material collected in the distillation of the product for each example are shown in the Table. The values under "Fresh Charge" include the amounts of fresh TMP and HCHO added in each example, the total benzene weight including the solvent recovered from the preceding example plus fresh benzene added to replace that lost during workup, and the amount of MSA added each time. No recycle of MSA was possible. The values under "Recycle" are the amounts of material in the distillation riser cut, or forerun, the distillation pot residue, and the material trapped in the vacuum distillation cold trap, most of which were recycled to the following example as part of its initial charge in addition to the fresh reagents charged. In each example, the heart cut from the distillation was collected as TMPF product, while the "heavier condensation products," as previously described, were concentrated in the residue.

Analysis of the heart cuts of these examples shown in the Table, using gas chromatography (GC) and nuclear magnetic resonance (NMR), indicated that they were composed of about 99% of TMPF with the remainder being mainly composed of the bicyclic linear formal of TMP (Formula VII). Based on these analyses, the overall efficiency of the production of TMPF resulting from Examples 1 to 6 was 94.6% based on TMP and 95.3% based on HCHO. Similar analyses of samples of the residues produced in the examples which were recycled to the following example indicated the presence of the bicyclic linear formal of TMP [Formula (VII)], and other "heavier condensation products" which are likely to comprise the compounds of Formulas (VIII) and (IX). In general, the results of the examples indicated that when the "heavier condensation products" of the residue was subjected to additional reaction after removal of the TMPF produced in the previous example, they reequilibrated to about 80% TMPF and about 20% of the heavier condensation products. Because of this, the foregoing efficiencies of overall TMPF production were much higher than if the heavier condensation products in the residue were discarded, on the assumption that they could not be reacted to produce additional TMPF.

EXAMPLES 7 AND 8

These examples illustrate the preparation of TMPF from TMP and formaldehyde from paraform using the general procedure of Example 1 except as follows: A 5 tray by 2 in. rather than a 10 tray by 3 in. Oldershaw column was employed. The reaction charge was 4294 g (32 moles) of TMP, 1045 g (32 moles) of formaldehyde, 3535 g of toluene, 1773 g of n-hexane, and 75.5 g of 70% MSA. These reagents were charged to the round bottom flask and heated at reflux with stirring for seven hours. Base temperatures varied from 75°-92° C. and overhead temperatures varied from 63°-69° C. Water was collected overhead until the rate of water removal became slow, and the theoretical yield of water had been obtained. After reaction, the crude reaction mixture was extracted with two 500 ml portions of aqueous 13% $Na_2CO_3$ and washed with distilled water. After neutralization, the product was purified by distillation using a single stage distillation apparatus. Most of the residual solvent was distilled off under medium vacuum conditions (100-140 mm HgA), after which the remaining product was distilled using a single stage distillation and high vacuum to obtain pure TMPF.

In Example 7, 260 g of solvent were taken off at 125 mm HgA and an overhead temperature of 81°-85° C., 202 g (4.3% of theoretical yield) of a riser forecut were taken off at a pressure of 12-25 mm HgA and an overhead temperature of 80°-122° C., and 3541 g (75.8% of theoretical yield) of a TMPF fraction were taken off at a pressure of 3-5 mm HgA and an overhead temperature of 106°-114° C., leaving a residue of 558 grams (11.9% of theoretical yield).

In Example 8, 240 g of solvent were taken off at a pressure of 115 mm HgA and an overhead temperature of 81=103° C., 375 g (8.0% of theoretical yield) of a riser forecut were taken off at a pressure of 8 mm HgA and an overhead temperature of up to 106° C., and 3228

TABLE

| Example | REACTOR CHARGE | | | | | | DISTILLATION | | |
|---|---|---|---|---|---|---|---|---|---|
| | FRESH CHARGE | | | | RECYCLE | | Heart Cut | | |
| | TMP g | HCHO g | Benzene g | MSA-70% g | Riser & Trap g | Residue g | (TMPF prod) g | Residue g | Riser & Trap g |
| 1 | 4751 | 1080 | 3936 | 49 | — | — | 4027 | 893 | 165 |
| 2 | 3945 | 906 | 3936 | 49 | 165 | 893 | 3870 | 1390 | 122 |
| 3 | 3440 | 775 | 3936 | 49 | 122 | 1324 | 3601 | 1380 | 122 |
| 4 | 0 | 0 | 1490 | 20 | 121 | 1369 | 571 | 847 | 30 |
| 5 | 0 | 0 | 872 | .9 | 29 | 843 | 62 | 776 | 16 |
| 6 | 292 | 0 | 1068 | 21 | 0 | 770 | 781 | 246 | 35 | g (69.2% of theoretical yield) of a TMPF fraction were taken off at a pressure of 4-5 mm HgA and an overhead temperature of 105°-115° C. leaving a residue of 520 g (11.1% of theoretical yield).

EXAMPLE 9

The procedure of Examples 7 and 8 was followed except that 1655 g (11.32 moles) of the total of the riser forecuts and residues of Examples 7 and 8 were also charged to the reactor with the other reagents. Solvent in an amount of 133 g was taken off at a pressure of 25-135 mm HgA and an overhead temperature of up to 94° C., 238 g (3.8% of theorectical yield) of a riser forecut were taken off at a pressure of 8-25 mm HgA and an overhead temperature of up to 115° C., and 4390 g (69.4% of theoretical yield) of a TMPF fraction were taken off at a pressure of 5-8 mm HgA and an overhead temperature of 112°-115° C. leaving a residue of 1259 g (19.9% of theoretical yield).

The cumulative yields of Examples 7, 8 and 9 were 238 g (1.63 moles, 1.7% of theoretical yield) of riser forecut, 11169 g (76.40 moles, 79.6% of theoretical yield) of a TMPF fraction, and 1259 g (8.61) moles, 9.0% of theoretical yield) of residue.

It is noteworthy that the yield of residue in Example 9 was less than the absolute amount of residue charged from the preceding two examples. This supports the conclusion that recycle of TMPF heavy ends serves to re-equilibrate the mixture of formals, as discussed previously.

EXAMPLE 10

This example illustrates the formation of trimethylol propane monocyclic formal acrylate (TMPFAcA) by the transesterification of TMPF with methyl acrylate (MeAcA) using tetra-isopropyl orthotitanate as transesterification catalyst and methyl ether of hydroquinone (MEHQ) as inhibitor.

The transesterification reaction employed a 3-liter flask equipped with a 40 tray by 1" Oldershaw column, thermometer well, mechanical stirrer, gas sparge inlet, sampling port, and additional port. An oil bath was used for heating.

TMPF (730 g, 5.0 mol) prepared with recycle of heavier condensation products as shown in Examples 2 to 6, MeAcA (603 g, 7.0 mol) and MEHQ (0.2 g, 200 ppm based on final product) were charged to the reactor which was sparged with nitrogen containing 10% $O_2$ at a rate of 0.25 standard cubic foot per hour (SCFH). The system was brought up to reflux and the boilup material was totally condensed in the overhead system on top of the Oldershaw column. An inlet port at tray 40 of the Oldershaw was used to add inhibitor to prevent MeAcA polymerization in the column (1000 ppm MEHQ in MeAcA, addition rate - 3 ml/hr). A sampling port at tray 30 was used to sample azeotropic composition. The liquid condensate flowed into a reservoir for return to the column overhead. The reservoir consisted of a calibrated receiver for measuring boil-up rates plus a receiver to collect the condensate when boil-up data was not being taken. The level of liquid in the reservoir was held constant with a liquid pump which was actuated by a level sensor attached to the reservoir.

Before the addition of the catalyst, wet methyl acrylate was removed from the liquid reservoir until the water content of the base dropped below 0.05% by weight. Water was removed to prevent hydrolytic decomposition of the tetraisopropyl orthotitanate catalyst to form catalytically inactive titanium dioxide. MeAcA was added from the MeAcA reservoir to replace that removed during drying.

The tetra-isopropyl orthotitanate catalyst (14.5 g, 1.25 wt.%) was added to the reaction vessel with a syringe through a rubber septum. The reaction was heated and stirred while the methanol of reaction was removed overhead as a methanol/methyl acrylate azeotrope, such removal being controlled by a temperature sensor located at tray 30 of the Oldershaw column. The temperature sensor activated a timer and a pump which removed azeotrope from the liquid reservoir when the temperature at tray 30 dropped below 65° C.

In steady state operation, the liquid in the reservoir was returned to the column overhead via a pump controlled by a level sensor. The level sensor and pump were adjusted to maintain a constant level of liquid in the reservoir and a constant flow of liquid returning to the overhead of the column. This liquid passed through a pre-heater which heated the return to 65° C. Methyl acrylate (MeAcA) was added during the course of the reaction to replace that removed as the azeotrope and that converted to TMPFAcA. MeAcA addition was controlled by temperature demand so as to maintain a constant temperature in the order of 85° C. in the base. Thus, the reaction temperature could be varied and controlled to some extent by varying the concentration in the base. The feed system consisted of an external MeAcA reservoir and a pump which was actuated by a temperature sensor which monitored the base temperature.

The reaction was continued until 99.5% of the starting TMPF was consumed, as indicated by a GC monitor. Reaction times were typically 12-13 hours depending on temperature and catalyst charge. After complete reaction, the catalyst was hydrolyzed by adding water (1 g per g catalyst) and the mixture was heated at 80°-85° C. for one hour, utilizing apparatus including the 3-liter flask equipped with reflux condenser, thermowell, gas sparge inlet, and mechanical stirrer. Catalyst hydrolysis was complete as evidenced by the light-yellow precipitate of amorphous, hydrated $TiO_2$.

Celite filter aid (1 g per g catalyst) was added and mixed thoroughly. The vacuum filtration step usually required 1 to 2 hours, and utilized a side-arm filtering flask equipped with a 3-liter sintered glass filter funnel. An air sparge (10% $O_2$) was discharged below the level of the filtrate (0.2 SCFH) to prevent degassing. The filter cake was washed with MeAcA and this extract was combined with the filtrate. Removal of the excess MeAcA with a rotary flash evaporator yielded TMPFAcA product. The evaporator was equipped with a bubbler tube discharging gas (10% $O_2$, 2SCFH) through the liquid in the flask and was operated at a pressure of about 100-150 mm Hg absolute. A water bath was used to maintain the flask temperature at 45°-50° C. during the stripping operation.

A final filtration of the product through a small Celite bed removed traces of particular matter.

The efficiency of production of TMPFAcA based on TMPF was found to be at least 95.6%, using the described transesterification procedure.

Examples 11 and 12 illustrate the preparation of trimethylol propane cyclic formal acetate (TMPFA) by reaction of TMPF and acetic anhydride in the presence of pyridine.

EXAMPLE 11

A three neck round bottom flask with mechanical stirrer, condenser, thermometer well, and heating bath was used for the reaction. The charge consisted of 439 g (3.00 moles) of TMPF prepared with recycle of heavier condensation product as shown in Example 9, 388 g (3.80 moles) of acetic anhydride, and 600 g (7.58 moles) of pyridine.

The mixture was reacted at room temperature for 29.5 hours, at which point there was still unconverted alcohol in the reactor. The mixture was then heated for an additional two hours at 66°-67° C. The resulting product was purified by distillation, with acetic anhydride, acetic acid and pyridine being first distilled off using a three liter round bottom flask equipped with a 1" by 5 tray Oldershaw column and reduced pressure (3-15 mm HgA) to keep the temperature of the distillation residue below about 70° C. The remaining mixture containing trimethylolpropane cyclic formal acetate (TMPFA) was then distilled using a single plate distillation apparatus. Initially, 26 g total (4.6% of theoretical yield) of a riser forecut and vacuum distillation cold trap fraction, were taken off at a pressure of 0.5-1.0 mm HgA and an overhead temperature of 70° C. Then 519 g (91.9% of theoretical yield) of a TMPFA fraction were taken off at a pressure of 1.0 mm HgA and a temperature of 78° C., leaving a residue of 29 g (5.1% of theoretical yield).

EXAMPLE 12

The procedure of Example 11 was followed except that the charge was 2193 g (15.0 moles) of the TMPF, 2231 g (21.9 moles) of acetic anhydride, and 3450 g (43.6 moles) of pyridine which were reacted for 70 h at room temperature. Initially, acetic anhydride, acetic acid, and pyridine were taken off at a pressure of 10-20 mm HgA and a base temperature of 60°-80° C. Then, using the single plate distillation apparatus, 613 g of a riser forecut were taken off at 10-20 mm HgA and an overhead temperature of 45°-112° C. Finally, 2527 g (89.5% of the theoretical yield) of a TMPFA fraction were taken off at a pressure of 10 mm HgA and an overhead temperature of 112-115° C. leaving a residue of 154 g.

EXAMPLE 13

This example illustrates the preparation of mixed glycerine cyclic formal acetates (MGFA) in accordance with the invention, using the general procedure of Examples 11 and 12.

The acetylation reaction was performed in a two liter round bottom flask equipped with a magnetic stirrer and an addition funnel. The charge consisting of 320 g (3.07 moles) of mixed glycerine cyclic formals (MGF), prepared with recycle of heavier condensation products as shown in Example 9, 510,5 g (5.0 moles) of acetic anhydride, and 790 g (10.0 moles) of pyridine, was placed in the reaction flask and stirred at room temperature for 119 hours. After the acetylation was complete, the mixture was purified by vacuum distillation performed in a round bottom flask equipped with a 1 in. distillation head (no distillation column), condenser, and heating mantle under reduced pressure. A light fraction of acetic anhydride, acetic acid, and pyridine were taken off first at a pressure of 60 mm HgA and a base temperature of 68-90° C. Then, 100 g of a riser forecut were taken off at an overhead temperature of 69°-135° C. Finally, 352 g (78.5% of theoretical yield) of a MGFA fraction were taken off, leaving 30 g of residue. In addition, 4 g of material were collected from the vacuum distillation cold trap.

The procedure of Examples 2 to 6 and 9 could also be used to produce the other monohydroxy monocyclic acetals contemplated under the invention, including TMP cyclic acetal, TMP cyclic propional, and TMP cyclic butyral, TME cyclic formal, TME cyclic propional, TME cyclic butyral, a mixture of glycerine-1,2-cyclic formal and glycerine-1,3-cyclic formal, (mixed glycerine cyclic formal), mixed glycerine cyclic acetal, mixed glycerine cyclic propional, and mixed glycerine cyclic butyral, the 1,2-cyclic formal of 1,2,6-hexanetriol, the 1,2-cyclic acetal of 1,2,6-hexanetriol, the 1,2-cyclic propional of 1,2,6-hexanetriol, and the 1,2-cyclic butyral of 1,2,6-hexanetriol. Obviously, the optimum ranges of conditions of the process may vary somewhat depending on the specific product being produced.

Esters other than TMPFAcA and contemplated under the invention could be produced using the procedure of Example 10 to 13, e.g., TMPF methacrylate, TMPF propionate, TME cyclic formal acrylate, TME cyclic formal methacrylate, TME cyclic formal acetate, TME cyclic formal propionate, mixed glycerine cyclic formal acrylate, mixed glycerine cyclic formal methacrylate, mixed glycerine cyclic formal acetate, mixed glycerine cyclic formal propionate, 4(4-hydroxybutyl)-1,3-dioxolane acrylate, 4(4-hydroxybutyl)-1,3-dioxolane methacrylate, 4(4-hydroxybutyl)-1,3-dioxolane acetate, and 4(4-hydroxybutyl)-1,3-dioxolane propionate.

As state previously, the esters of cyclic acetals with unsaturated acid contemplated by the process of this invention are suitable for use as monomers in the production of a variety of polymer products, including, in particular, ultraviolet curable coating compositions as disclosed, for example, in the previously cited U.S. patents.

The free cyclic acetals and esters of such cyclic acetals with saturated and unsaturated acids contemplated by the process of this invention may be used, for example, to produce acetal polymers having certain functional side groups, e.g., by copolymerization with trioxane.

We claim:

1. A process for the production of a monohydroxy monocyclic acetal of a trihydroxy alcohol selected from the group consisting of trimethylolpropane, trimethylolethane and compounds of the formula:

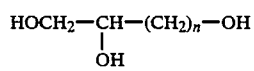

where n is 1 to 4, with an aldehyde having the formula:

where R' is hydrogen, $C_1$-$C_3$ alkyl, or $C_1$-$C_3$ halogenated alkyl, by subjecting to acetal formation conditions an initial feed composition comprising at least one condensation product of said trihydroxy alcohol and said aldehyde having a higher molecular weight and higher boiling point than said monohydroxy monocyclic acetal.

2. The process of claim 1 wherein said monohydroxy monocyclic acetal is trimethylolpropane cyclic formal, said trihydroxy alcohol is trimethylolpropane and said aldehyde is formaldehyde.

3. A process comprising reacting a composition comprising a trihydroxy alcohol selected from the group consisting of trimethylolpropane, trimethylolethane and compounds of the formula:

$$HOCH_2-\underset{\underset{OH}{|}}{CH}-(CH_2)_n-OH$$

where n is 1 to 4, with an aldehyde having the formula:

R'CHO where R' is hydrogen, $C_1$-$C_3$ alkyl, or $C_1$-$C_3$ halogenated alkyl, to produce a monohydroxy monocyclic acetal and at least one heavier condensation product having a higher molecular weight and higher boiling point than said monohydroxy monocyclic acetal, separating said monohydroxy monocyclic acetal from said heavier condensation product, and subjecting at least part of said heavier condensation product to acetal formation conditions to produce an additional amount of said monohydroxy monocyclic acetal.

4. The process of claim 3 wherein said heavier condensation product is subjected to acetal formation conditions in the presence of an additional supply of said trihydroxy alcohol and aldehyde.

5. The process of claim 4 wherein the resultant product is withdrawn from the zone of said reaction and separated into said monohydroxy monocyclic acetal and heavier condensation product, and said heavy condensation product is recycled to the reaction zone together with a fresh supply of said trihydroxy alcohol and aldehyde.

6. The process of claim 4 wherein said trihydroxy alcohol is trimethylolpropane, said aldehyde is formaldehyde, and said monohydroxy monocyclic acetal is trimethylolpropane cyclic formal.

7. The process of claim 5 wherein said separated monohydroxy monocyclic acetal is transesterified using tetra-isopropyl orthotitanate as catalyst with an alkyl ester of an esterifying acid selected from the group consisting of acrylic acid, methacrylic acid and alkanoic acids containing 1 to 4 carbon atoms, to produce a corresponding ester of said monohydroxy monocyclic acetal.

8. The process of claim 7 wherein said monohydroxy monocyclic acetal is trimethylolpropane cyclic formal, said alkyl ester is methyl acrylate and said ester of said monohydroxy monocyclic acetal is trimethylolpropane cyclic formal acrylate.

9. The process of claim 5 whrein said separated monohydroxy monocyclic acetal is esterified with the anhydride of an esterifying acid in the presence of pyridine.

10. The process of claim 9 wherein said monohydroxy monocyclic acetal is a monohydroxy monocyclic formal and said esterifying acid is acetic acid.

11. The process of claim 10 wherein said monohydroxy monocyclic formal is trimethylol propane cyclic formal.

12. The process of claim 10 wherein said monohydroxy monocyclic formal is a mixed glycerine cyclic formal.

* * * * *